(12) United States Patent
Hautvast

(10) Patent No.: US 11,213,700 B2
(45) Date of Patent: Jan. 4, 2022

(54) BRACHYTHERAPY AFTERLOADER DEVICE

(71) Applicant: KONINKLIJKE PHILIPS N.V., Eindhoven (NL)

(72) Inventor: Guillaume Leopold Theodorus Frederik Hautvast, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/462,568

(22) PCT Filed: Oct. 19, 2018

(86) PCT No.: PCT/EP2018/078667
§ 371 (c)(1),
(2) Date: May 21, 2019

(87) PCT Pub. No.: WO2019/081357
PCT Pub. Date: May 2, 2019

(65) Prior Publication Data
US 2020/0254281 A1 Aug. 13, 2020

(30) Foreign Application Priority Data
Oct. 26, 2017 (EP) .................... 17198449

(51) Int. Cl.
*A61N 5/10* (2006.01)
*G01D 5/14* (2006.01)

(52) U.S. Cl.
CPC .......... *A61N 5/1075* (2013.01); *A61N 5/1007* (2013.01); *G01D 5/14* (2013.01); *A61N 2005/1008* (2013.01)

(58) Field of Classification Search
CPC .......... A61N 2005/1008; A61N 5/1001–1029; A61N 5/1048–1049; A61N 5/1075
See application file for complete search history.

(56) References Cited

U.S. PATENT DOCUMENTS 5,957,829 A * 9/1999 Thornton ............. A61N 5/1007
600/3
6,266,552 B1 7/2001 Slettenmark
(Continued)

FOREIGN PATENT DOCUMENTS

EP 1745820 A1 1/2007

OTHER PUBLICATIONS

International Search Report—PCT/EP2018/078667, filed Oct. 19, 2018.

*Primary Examiner* — Thaddeus B Cox
(74) *Attorney, Agent, or Firm* — Sherry Austin

(57) ABSTRACT

A brachytherapy afterloader device, comprises at least one transmit wire that is suitable for being inserted and driven in an advance or retract motion in an external first delivery channel and for delivering drive energy to a test field source, which is arranged at a distal end region of the transmit wire, for generating a magnetic test field; at least one receive wire that is suitable for being inserted and driven in an advance or retract motion in an external second delivery channel for a measurement of the magnetic test field, the receive wire having a transducer that is configured to detect magnetic-field changes in the magnetic test field; and a wire driving unit which is configured to controllably advance or retract the transmit wire and the receive wire in response to a corresponding test drive control signal.

14 Claims, 6 Drawing Sheets

(56) References Cited

U.S. PATENT DOCUMENTS

| | | | |
|---|---|---|---|
| 9,364,685 B2 | 6/2016 | Kindlein | |
| 2006/0258895 A1 | 11/2006 | Maschke | |
| 2007/0078327 A1* | 4/2007 | Kindlein | A61N 5/1007 600/407 |
| 2010/0312038 A1* | 12/2010 | Shechter | A61N 5/1015 600/3 |
| 2014/0350325 A1 | 11/2014 | Van Appeldoorn et al. | |
| 2014/0357977 A1 | 12/2014 | Zhou | |
| 2015/0051861 A1 | 2/2015 | Kruecker et al. | |
| 2015/0246247 A1 | 9/2015 | Binnekamp et al. | |
| 2016/0166328 A1 | 6/2016 | De Vries et al. | |
| 2016/0339267 A1 | 11/2016 | Woudstra et al. | |
| 2017/0007849 A1* | 1/2017 | Hautvast | A61N 5/1001 |
| 2017/0368368 A1* | 12/2017 | Bharat | A61N 5/1048 |

* cited by examiner

BRACHYTHERAPY AFTERLOADER DEVICE

CROSS REFERENCE TO RELATED APPLICATIONS

This application is a U.S. national phase application of International Application No. PCT/EP2018/078667 filed on Oct. 19, 2018, which claims the benefit of EP Application Serial No. 17198449.5 filed on Oct. 26, 2017 and is incorporated herein by reference.

FIELD OF THE INVENTION

The present invention is directed to a brachytherapy afterloader device, to a brachytherapy system, to a method for operating an afterloader control unit of a brachytherapy system and to a computer program.

BACKGROUND OF THE INVENTION

In brachytherapy, cancer is treated by delivering radiation to a target area using a brachytherapy afterloader device that serves to store one or more radioactive sources, each positioned on a respective wire. Such a brachytherapy afterloader device will also be referred to herein in short as an afterloader device or an afterloader.

In response to suitable control signals the afterloader drives a desired wire through an implanted catheter or delivery channel to position the radioactive source in a desired treatment position, and after treatment retracts the wire to place the radioactive source back in a storage position or drive it into another catheter or, more generally speaking, delivery channel for further treatment according to a brachytherapy treatment plan.

Known afterloader devices typically either include or are attached to a selector mechanism such as an indexing unit that is configured to select which wire is to be introduced into which channel or catheter. Typically, a wire can be connected via the indexing unit to any one of a plurality of delivery channels that are placed so as to cover a predetermined target volume with a desired radiation dose according to a predetermined brachytherapy treatment plan. The number of delivery channels commonly ranges from 2 to 40. The indexing unit thus allows the use of afterloaders comprising for instance only one highly radioactive source that is sequentially inserted into two more delivery channels according to a predetermined brachytherapy treatment plan.

US 2014/0350325 A1 describes such an afterloader device for effecting a brachytherapy treatment. That afterloader device comprises a first elongated flexible transport element such as a wire, arranged to maneuver a radiation source between a storage position inside the afterloader device and a treatment position outside the afterloader. The known afterloader device also comprises a second elongated flexible transport element having a transducer for detecting radiation emitted by the radiation source and arranged to move the at least one transducer between a first transducer position and a second transducer position. The afterloader device known from US 2014/0350325 A1 provides a quality assurance feature by using the transducer to achieve an in-situ detection of discrepancies between a measured transducer signal and an expected transducer signal according to the predetermined brachytherapy treatment plan during the treatment.

SUMMARY OF THE INVENTION

It would be beneficial to provide an afterloader with capability for supporting improved quality assurance.

According to a first aspect of the present invention, a brachytherapy afterloader device is presented, the brachytherapy afterloader device comprising:

at least one transmit wire that is suitable for being inserted and for being driven in an advance or retract motion in an external first delivery channel, the transmit wire having a test field source, which is arranged at a distal end region of the transmit wire, for controllably providing a magnetic test field;

at least one receive wire that is suitable for being inserted and for being driven in an advance or retract motion in an external second delivery channel for a measurement of the magnetic test field, the receive wire having a transducer that is configured to detect magnetic-field changes in the magnetic test field and to provide a transducer signal indicative thereof via the receive wire;

a wire driving unit which is configured to controllably advance or retract the transmit wire and the receive wire in response to receiving a corresponding drive control signal.

The brachytherapy afterloader device of the first aspect of the invention thus comprises a test field source that is located at a distal end region of a transmit wire. The test field source is electrically controllable and configured to generate a magnetic test field. As a test field, the magnetic test field is not intended to have any curative or therapeutic effect on a patient. A transducer located on a receive wire is configured to detect magnetic-field changes and to provide a transducer signal indicative thereof. The brachytherapy afterloader device further comprises a wire driving unit, which is configured to drive a controlled movement of the transmit wire and the receive wire. To this end, the wire driving unit is advantageously configured to controllably advance or retract the transmit wire, the receive wire or both the transmit wire and the receive wire in response to receiving a corresponding drive control signal. Therefore, the wire driving unit is advantageously configured to controllably alter a position of the test field source and a position of the transducer.

The wire driving unit serves to control a relative spatial positioning or a relative motion between the test field source and the transducer in dependence on the received test drive control signal. A transducer signal indicative of detected magnetic-field variations comprises information on the relative positioning of the transducer and the test field source with respect to each other.

By providing the transmit wire with the non-therapeutic test field source that generates a non-therapeutic magnetic test field, and by providing the receive wire with the transducer that delivers the transducer signal indicative of magnetic-field changes of the magnetic test fields, and by controlling the positioning and motion of the transmit wire and the receive wire using the wire driving unit, the brachytherapy afterloader device of the present invention advantageously provides capabilities for any desired test operation that allows a test evaluation of afterloader functionalities or external therapy settings without having to use a radioactive source. This forms an improvement in quality assurance.

In the following, different embodiments of the brachytherapy afterloader device of the first aspect will be described.

A suitable test field source can be selected as any magnetic field source which has extensions allowing for insertion and motion in a given (first) delivery channel to be used for the test, and which has a spatial magnetic-field extension and thus a field amplitude strong enough for detection of field changes by the transducer. The test field source can for instance be a permanent magnet.

In other embodiments, the test field source is a magnetic field source configured to generate the magnetic test field in dependence on electrical drive energy. In these embodiments, the transmit wire is configured to transport the electrical drive energy from an external electrical energy supply device to the test field source.

Preferably, in some of these embodiments the test field source comprises a transmit coil, and the transducer comprises a receive coil. The electromagnetic generation and detection principle employed in this embodiment allows making use of different variants, for instance by driving the test field source to produce a time-varying magnetic test field and/or by driving the transmit and/or receive wires to produce a time-varying relative positioning of the test field source and the transducer. This will be addressed in more detail further below.

The transmit and receive wires preferably comprise respective connecting wires in a respective inner lumen of the transmit and receive wires. The connecting wires are arranged to electrically connect the receive coil with an external signal receiving unit for receiving the transducer signal, and the transmit coil with an external transmit-coil driving unit for delivering the electrical drive energy, respectively.

In other embodiments of the afterloader, the wire-driving unit comprises:
a transmit-wire reel for accommodating at least a portion of the transmit wire in its retracted state;
a receive-wire reel for accommodating at least a portion of the receive wire in its retracted state;
a first motor configured to drive the transmit-wire reel in effectuating the advance or retract motion of the transmit wire in response to a corresponding first test drive control signal; and
a second motor configured to drive the receive-wire reel in effecting the advance or retract motion of the receive wire to a corresponding second test drive control signal.

The afterloader device of the first aspect of the invention can be provided as a stand-alone afterloader testing module that only has the transmit wire and the receive wire, and no therapy wire. Such afterloader devices can be used as an add-on module for extending the functionality of prior-art afterloader devices.

However, preferred embodiments of the brachytherapy afterloader device further comprise at least one therapy wire that is suitable for being inserted and for being driven in an advance or retract motion in at least the first external delivery channel and comprising a radioactive source, which is arranged at a distal end region of the therapy wire. In these embodiments, the wire driving unit is additionally configured to controllably advance or retract the therapy wire in response to a corresponding therapy drive control signal.

It will be appreciated that the afterloader device of the first aspect of the invention may comprise more than one transmit wire and thus more than one test field source. Also, embodiments of the afterloader device have more than one receive wire and thus more than one transducer. The use of more than one transducer in different positions is advantageous in particular for quickly performing a precise position detection of the test field source. Yet other embodiments have more than one transducer on the same receive wire. With each transducer delivering its own transducer signal, more information on the position of the test field source can be obtained.

According to a second aspect of the present invention, a brachytherapy system is provided. The brachytherapy system comprises a brachytherapy afterloader device according to any of the embodiments of the present invention and an afterloader control unit that comprises:
a test drive control unit configured to provide, using planned-therapy data indicative of at least of a planned radioactive-source position in the first delivery channel, the test drive control signal to the wire driving unit for positioning the test field source at a test position depending on the planned radioactive-source position in the first external delivery channel, and for positioning the transducer at at least one receive position in the at least one second external delivery channel;
a signal receiving unit that is configured to sample the transducer signal provided by the transducer in the at least one receive position in the second external delivery channel via the receive wire; and
a quality-assurance unit that is connected with the signal receiving unit and configured to
determine, using the test position and the at least one receive position in the at least one second external delivery channel, at least one expected transducer signal to be expected from the transducer at the at least one receive position when the test field source is at the test position, and
perform a comparison of the received transducer signal with the expected transducer signal and provide a quality assurance signal indicative of a result of the comparison.

The brachytherapy system of the second aspect implements an improved quality assurance feature. Prior-art afterloader systems in operation are not aware of an actual exact three-dimensional position of the radioactive source. The actual position may deviate from the desired position for a number of reasons. A known error scenario is for instance an unintentional exchange of two catheters, which leads to strong differences between planned and actual treatment. Therefore, the exact dose delivered remains uncertain. The in vivo dosimetry concept for quality assurance known from US 2014/0350325 A1 enables measuring the delivered dose. However, that technology is only helpful in reporting on treatment, as an incorrectly delivered dose cannot be corrected once it has been measured by an in vivo dosimetry device. In the worst case, therefore, even tissue damage by an incorrect dose delivery would be detected, but not avoided. In contrast, the quality assurance concept of the brachytherapy system of the second aspect of the invention can be used for performing extensive testing before actual treatment is started, without risking any damage to the patient.

In the following, embodiments of the brachytherapy system of the second aspect will be described.

As briefly indicated above, the testing scheme can be implemented in different ways, which will now be described in more detail.

In preferred embodiments of the brachytherapy system, the transmit wire of the afterloader device is configured to transport electrical drive energy to the test field source, which in turn is configured to generate the magnetic test field in dependence of the electrical drive energy received, and the brachytherapy system also comprises a test-field-source driving unit configured to provide the electrical drive energy via the transmit wire for driving the test field source in generating the magnetic test field at the test position.

In some embodiments of the brachytherapy system of the second aspect, for controlling a respective measurement of the magnetic test field, the test drive control unit is configured to provide the test drive control signal to the wire driving unit in a manner that is suitable for positioning the test field source at one predetermined test position and for consecutively positioning the transducer at a plurality of receive positions in the second external delivery channel; or for consecutively positioning the test field source at a plurality of predetermined test positions and for positioning the transducer at one receive position in the second external delivery channel; or for consecutively positioning the test field source at a plurality of predetermined test positions and for simultaneously and consecutively positioning the transducer at a plurality of receive position in the second external delivery channel.

In different variants, the consecutive positioning is performed as discontinuous motion or as a continuous motion of the test field source or the transducer, respectively. A system using discontinuous motion performs the measurement of the test field with the test field source and/or the transducer at a fixed position, and then moves on to the next measurement position. A system using continuous motion generates the transducer signal while either the transducer or the test field source or both are in motion.

In some of these embodiments, the test field source is driven by electrical drive energy provided by a test-field-source driving unit, which provides, in a subset of these embodiments, an AC electric current for driving the generation of the magnetic test field. In other subset of these embodiments, the test-field-source driving unit is configured to provide a DC electric current for driving the test field source in generating the magnetic test field. The resulting magnetic test field is (in a steady state) substantially constant in magnitude and variations on the magnetic test field are detected by varying the position of either the test field source or of the transducer. In yet other embodiments, the test-field-source driving unit is configured to provide the electric drive signal as an electric current having a controllable current-amplitude value, a controllable current-frequency value and a controllable current-phase value. In yet other embodiment, the test-field-source driving unit is configured to generate a respective electric drive signal of a same or a different nature (i.e. AC electric current, DC electric current, variable electric current, etc.) at each testing location. In other embodiments for implementing a testing scheme, i.e., for controlling a respective measurement of the magnetic test field, the test drive control unit is configured to provide the test drive control signal to the wire driving unit for positioning the test field source at one predetermined test position and for positioning the transducer at one predetermined receive position in the second external delivery channel. The test-field-source driving unit of this embodiment is preferably configured to provide an AC electric current for driving the test field source in generating the magnetic test field.

In yet other embodiments of the brachytherapy system implementing a testing scheme, the test drive control unit is configured to provide the test drive control signal to the wire driving unit for consecutively positioning the transducer in a plurality of second external delivery channels, for controlling a plurality of consecutive measurements of the magnetic test field.

In other embodiments of the brachytherapy system of the present invention, the quality-assurance unit is configured to determine a signal amplitude of the received transducer signal and of the expected transducer signal, perform the comparison by determining a deviation measure indicative of a deviation of the signal amplitude of the received transducer signal from that of the expected transducer signal, provide the quality assurance signal as a positioning error signal if the deviation measure exceeds a predetermined deviation threshold value.

These embodiments generate the quality assurance signal as a warning signal indicative of a detection of a positioning error that may indicate to the operator that the desired treatment plan is not implemented as desired. For instance, the afterloader may have inserted the test field source to an incorrect channel, while the transducer has been inserted correctly in the pre-determined channel. In this situation, the transducer signal will show a deviation from the expected signal, which is indicative of an incorrect relative positioning of the test field source and the transducer.

According to a third aspect of the present invention, a method for operating an afterloader control unit of a brachytherapy system is presented. The method comprises:

controlling an advance or retract motion of at least one transmit wire that is suitable for being inserted and for being driven in an external first delivery channel for positioning the test field source at a predetermined test position in the first delivery channel;

controlling an advance or retract motion of at least one receive wire that is suitable for being inserted and for being driven in at least one external second delivery channel for positioning a transducer, that is arranged on the receive wire and configured to detect magnetic-field changes in the magnetic test field, at a predetermined receive position;

receiving from the transducer a transducer signal indicative of the detected magnetic-field changes.

The method of the third aspect shares the advantages of the afterloader device of the first aspect of the invention.

An embodiment of the method of the third aspect further comprises controlling delivery of electrical drive energy to a test field source which is arranged at a distal end region of the transmit wire, for controllably generating a magnetic test field;

Another embodiment of the method of the third aspect further comprises:

providing planned-therapy data indicative at least of a planned radioactive-source position in the first delivery channel;

determining, using the test position and the at least one receive position in the at least one second external delivery channel, at least one expected transducer signal to be expected from the transducer at the at least one receive position when the test field source is at the test position;

performing a comparison of the received transducer signal with the expected transducer signal; and providing a quality assurance signal indicative of a result of the comparison.

According to a fourth aspect of the present invention a computer program comprising instructions which, when the program is executed by a computer, cause the computer to carry out the method of the third aspect or any of its embodiments is provided.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
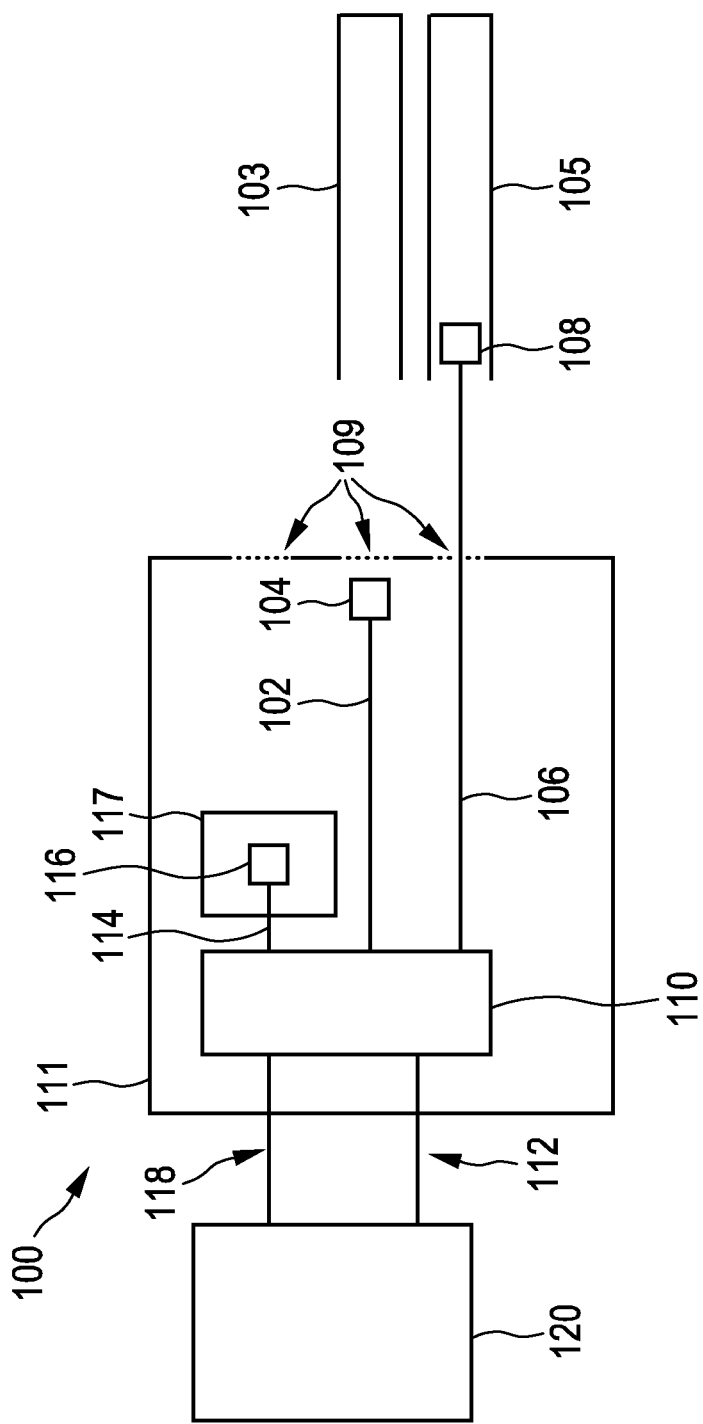
FIG. 1 shows a schematic representation of an embodiment of a brachytherapy afterloader device connected to an external afterloader control unit and two external delivery channels.

FIG. 1 shows a schematic representation of an embodiment of a brachytherapy afterloader device 100 connected to an afterloader control unit 120. The brachytherapy afterloader device, also referred to as an afterloader device or afterloader, comprises one transmit wire 102 that is suitable for being inserted and for being driven in an advance or retract motion in an external first delivery channel 103. The transmit wire 102 has a test field source 104 that is arranged at a distal end region of the transmit wire 102. The afterloader device also comprises one receive wire 106 that is suitable for being inserted and for being driven in an advance or retract motion in at least one external second delivery channel 105 for a measurement of the magnetic test field. The receive wire 106 has a transducer 108 that is configured to detect magnetic-field changes in the magnetic test field and to provide a transducer signal indicative thereof via the receive wire. Further, the afterloader device comprises a wire driving unit 110 which is configured to controllably advance or retract the transmit wire 102 and the receive wire 106 in response to a corresponding test drive control signal 112. The test drive control signal may comprise a plurality of individual signals directed to drive a respective one of the transmit or receive wire.

The afterloader device comprises a housing 111 that includes openings 109 to allow driving the transmit and the receive wires to positions both inside and outside the housing 111.

In preferred brachytherapy afterloader devices, such as the one described with reference to FIG. 1, the test field source 104 is electrically controllable to generate a magnetic test field in response to the delivery of electrical drive energy. In these cases, the transmit wire is suitable configured to transport electrical drive energy from an external energy source device to the test field source. In alternative afterloader devices, the test field source is a permanent magnet that does not require electrical drive energy to generate the magnetic test field.

In general, the position at which the test field source is located when generating the magnetic test field is controlled by the wire driving unit 110 in response to a corresponding drive control signal 112. Analogously, the position of the receive wire 106 with the transducer 108 is also controlled by the wire driving unit. The magnetic field variations detected by the transducer 108 and the corresponding transducer signal depend, among other parameters on the relative positions of the transducer 108 and the test field source 104, and information regarding a particular relative positioning of the transducer and the test field source can be advantageously extracted from the transducer signal.

Some afterloader devices, such as the one described with reference to FIG. 1 further comprises a therapy wire 114 that also is suitable for being inserted and for being driven in an advance or retract motion in at least the first external delivery channel 103. The therapy wire comprises a radioactive source 116, which is arranged at a distal end region of the therapy wire. In this case, the wire driving unit 110 is also configured to controllably advance or retract the therapy wire in response to a corresponding therapy drive control signal 118 that is in accordance with a predetermined therapy or treatment plan that is implemented by planned therapy data indicative of at least a planned radioactive-source position in the first delivery channel. When the therapy wire 114 is in a retracted state inside the housing 111, the radioactive source is located inside a radiation source storage unit 117 that is configured to shield the radioactive source and avoid detrimental radiation of the rest of the components of the afterloader device.

A given delivery channel usually comprises a catheter configured to be inserted into a target volume of a living being and a transfer tube for connecting the catheter to the afterloader device.

Figure 2:
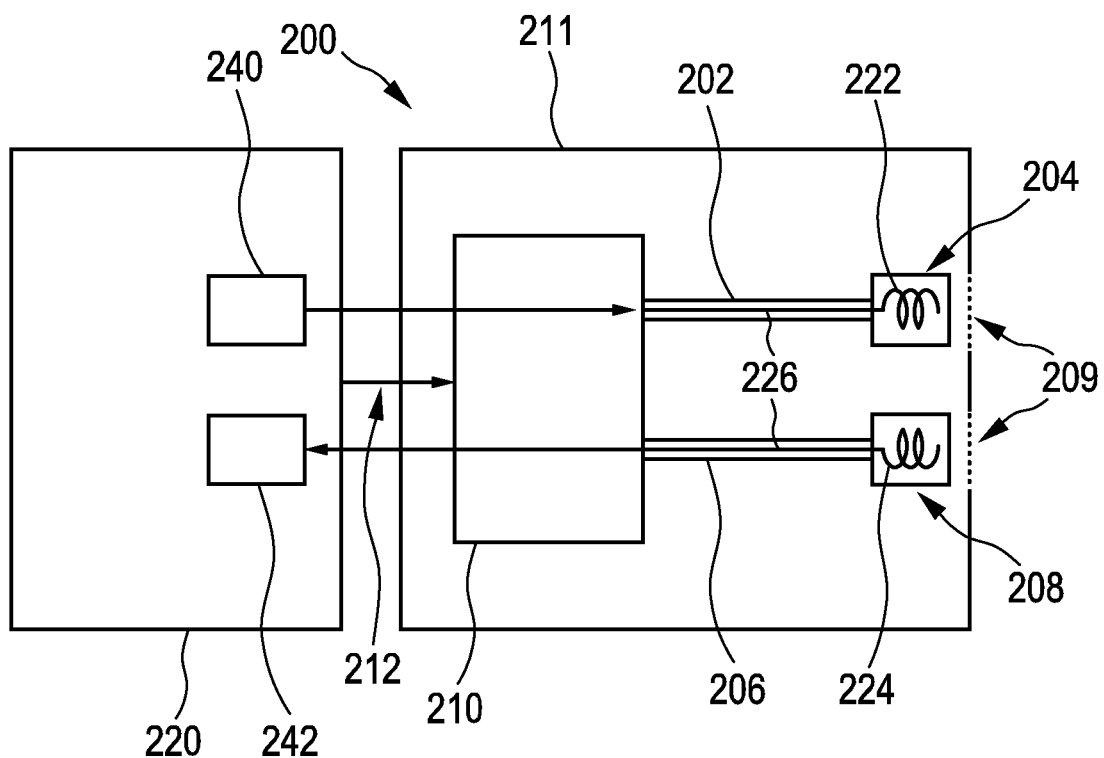
FIG. 2 shows a schematic representation of another embodiment of a brachytherapy afterloader device connected to an external afterloader control unit.

FIG. 2 schematically represents another embodiment of a brachytherapy afterloader device 200. The following discussion will focus on the features differentiating the afterloader device 100 described with reference to FIG. 1 and the present afterloader device 200. Similar features thus share the same numeral except the first digit, which is "1" in the case of features of the afterloader device 100 and "2" in the case of features included in the afterloader device 200.

The test field source 204 of the brachytherapy afterloader device 200 comprises a transmit coil 222 suitable for generating a magnetic test field when driven by electrical drive energy. The electrical drive energy is provided by an external transmit-coil driving unit 240 that in this particular example forms part of the afterloader control unit 220. The transmit-coil driving unit 240 is thus configured for controllably driving the transmit coil into generating the magnetic test field. Similarly, the transducer 208 comprises a receive coil 224 that is electrically connected to an external signal receiving unit 242 that is configured to receive the transducer signal, and that in the case also forms part of the afterloader control unit 220. The transmit wire 202 and the receive wire 206 comprise respective connecting wires 226 that are arranged in a respective inner lumen of the transmit and receive wires. The connecting wires are configured to electrically connect the receive coil 224 with the external signal receiving unit 242 for receiving the transducer signal, and the transmit coil 222 with the external transmit-coil driving unit 240 for delivering the electrical drive energy.

In some afterloader control units 220, the transmit-coil driving unit 240 is configured to provide an AC electrical current for driving the transmit coil 222 into generating the magnetic field. Other afterloader control units include transmit-coil driving units configured to provide a DC electrical current for driving the transmit coil into generating the magnetic field. Other embodiments include transmit-coil driving units capable of providing both AC and DC electrical current for controlling the generation of the magnetic test field.

Some afterloader devices such as the one described with reference to FIG. 2 also comprise a therapy wire and a radioactive source (not shown), and the corresponding wire driving unit 210 is configured to controllably advance or retract the therapy wire in response to a corresponding therapy drive control signal (not shown).

Figure 3:
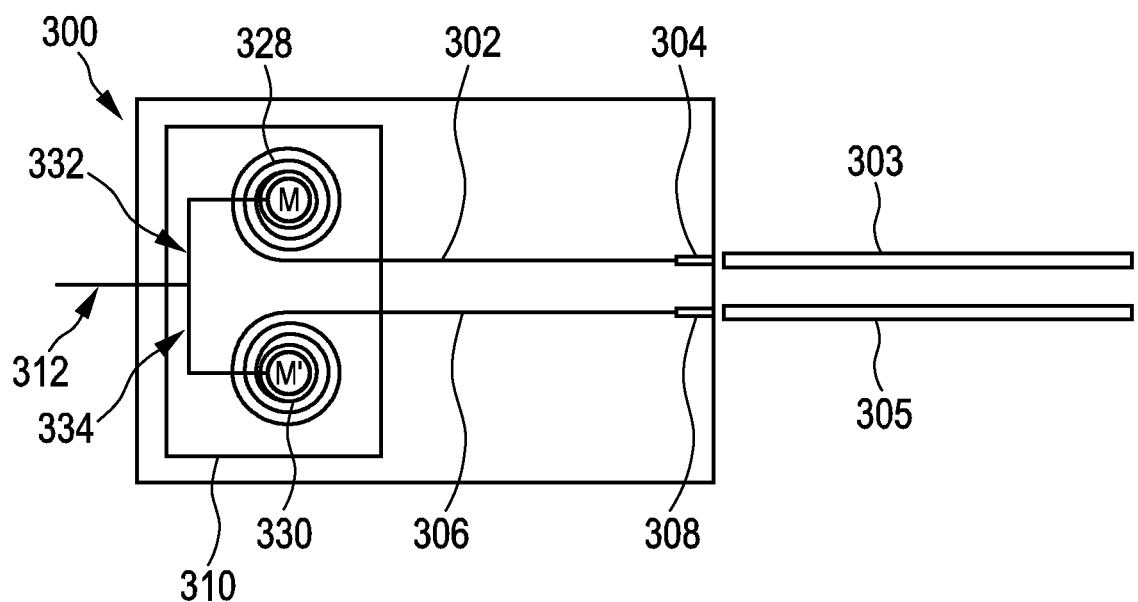
FIG. 3 shows a schematic representation of an embodiment of a brachytherapy afterloader and two external delivery channels.

FIG. 3 shows a schematic representation of an embodiment of a brachytherapy afterloader device 300 and two external delivery channels 303 and 305 for implantation in a target volume of a living being. Here again, the following discussion will focus on the features differentiating the brachytherapy afterloader devices 100 and 200 described with reference to FIGS. 1 and 2 and the present afterloader device 300. Similar features thus share the same numeral except the first digit, which is "1" in the case of features of the afterloader device 100 "2" in the case of features included in the afterloader device 200, and "3" for features of the afterloader device 300.

The wire-driving unit 310 of the afterloader device 300 includes a transmit-wire reel 328 for accommodating at least a portion of the transmit wire 302 in its retracted state. It also comprises a receive-wire reel 330 for accommodating at least a portion of the receive wire 306 in its retracted state. The wire-driving unit 310 also comprises a first motor M configured to drive the transmit-wire reel in effectuating the advance or retract motion of the transmit wire in response to a corresponding first test drive control signal 332 and a second motor M' configured to drive the receive-wire reel in effectuating the advance or retract motion of the receive wire to a corresponding second test drive control signal 334. The first and second drive control signals form part of the drive control signal 312. The motors M and M' are advantageously configured to drive a rotating movement of the respective reels 328 and 330 in both opposite directions (i.e. thus enabling the advancement and retraction of the transmit wire 302 and the receive wire 306).

Some afterloader devices such as the one described with reference to FIG. 3 also comprise a therapy wire and a radioactive source (not shown), and the corresponding wire driving unit 310 is configured to controllably advance or retract the therapy wire in response to a corresponding therapy drive control signal (not shown).

Figure 4:
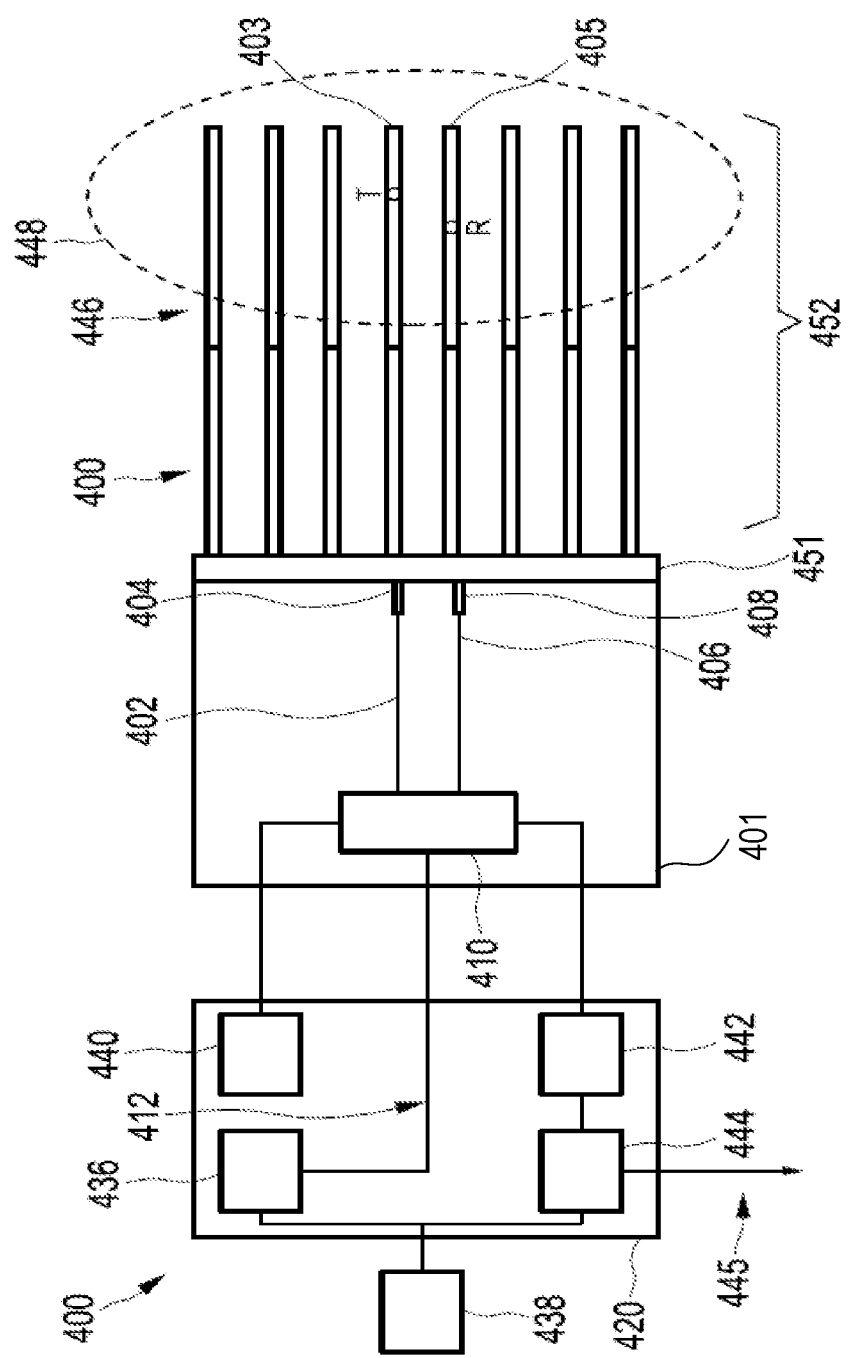
FIG. 4 shows a schematic representation of an embodiment of a brachytherapy system connected via an indexing unit to a plurality of delivery channels comprising catheters inserted into a target volume of a living being.

FIG. 4 shows a schematic representation of an embodiment of a brachytherapy system 400 connected via an indexing unit 451 to a plurality of delivery channels 452 comprising catheters 446 inserted into a target volume of a living being 448. The catheters 446 are connected to the indexing unit 451 via flexible transfer tubes 400. A catheter and the corresponding transfer tube form a respective delivery channel.

The brachytherapy system comprises an afterloader device 401 and an afterloader control unit 420. The afterloader device 401 can be connected to an indexing unit 451 having a plurality of openings to which one of a respective delivery channel such as delivery channel 403 or delivery channel 405 can be attached. The indexing unit thus enables the connection of a given wire (the transmit or the receive wire, or the therapy wire in afterloader devices that include it) to one of a plurality of delivery channels. The position of the transducer and the position of the test field source inside a respective delivery channel are controlled by the wire-driving unit 410 that drives an advancement or retraction of the corresponding wire. Here again, the features of the brachytherapy afterloader device 401 that are equivalent to those of the brachytherapy afterloader devices 100, 200 and 300 described with reference to FIGS. 1, 2 and 3 share the same numeral except the first digit, which is "1", "2" and "3" in the case of features of the afterloader devices 100, 200 and 300 respectively and "4" in the case of features included in the afterloader device 400.

The afterloader control unit 420 can be used with any of the afterloader devices 100, 200 or 300, described with reference to FIGS. 1-3. The afterloader control unit comprises a test drive control unit 436 configured to provide, using planned-therapy data 438 that is indicative of at least a planned radioactive-source position in the first delivery channel 403, the test drive control signal or signals 412 to the wire driving unit 410 for positioning the test field source 404 at a test position T. The test position T depends on the planned radioactive-source position in the first external delivery channel but does not necessarily have to be the same exact position. The test drive control signal or signals are also suitable for positioning the transducer 408 at at least one receive position R in the at least one second external delivery channel 405.

The afterloader control 420 unit also comprises a test-field-source driving unit 440 that is configured to provide the electrical drive energy via the transmit wire 402 for driving the test field source in generating the magnetic test field at the test position T.

Further, the afterloader control unit 420 comprises a signal receiving unit 442 that is configured to sample the transducer signal provided by the transducer 408 in the at least one receive position R in the second external delivery channel 405 via the receive wire 406, and also includes a quality-assurance unit 444 that is connected with the signal receiving unit.

The quality-assurance unit 444 is configured to determine, using the test position T and the at least one receive position R, at least one expected transducer signal to be expected from the transducer at the at least one receive position when the test field source is at the test position, and to perform a comparison of the received transducer signal with the expected transducer signal and provide a quality assurance signal indicative of a result of the comparison.

For controlling a respective measurement of the magnetic test field, different test drive control unit 436 are configured to provide test drive control signal or signals that are indicative of a particular wire-movement pattern of the transmit and the receive wire. In some brachytherapy systems, the provided test drive control signal or signals is suitable for positioning the test field source 404 at one predetermined test position T and for consecutively positioning the transducer 408 at a plurality of receive positions in the second external delivery channel 405. According to this particular wire-movement pattern, for a given measurement of the magnetic test field, the test field source remains fixed at the testing position whereas the transducer is consecutively positioned at a plurality of receive positions for detecting changes in the magnetic test field.

Other test drive control units are configured to additionally or alternatively provide test drive control signal or signals for consecutively positioning the test field source 404 at a plurality of predetermined test positions and for positioning the transducer 408 at one receive position R in the second external delivery channel 405. According to this particular wire-movement pattern, for a given measurement of the magnetic test field, the transducer remains fixed at the receiver position whereas the test field source is consecutively positioned at a plurality of testing positions.

Yet other test drive control units are configured to additionally or alternatively provide test drive control signal for consecutively positioning the test field source 404 at a plurality of predetermined test positions and for simultaneously and consecutively positioning the transducer at a plurality of receive position in the second external delivery channel 405. According to this particular wire-movement pattern, for a given measurement of the magnetic test field, the transducer remains and the test field source are consecutively positioned at a plurality of receiving and testing positions respectively.

In some of these brachytherapy systems, the test-field-source driving unit is configured to provide an AC electric current for driving the test field source in generating the magnetic test field. Alternatively, in some of these brachytherapy systems, the test-field-source driving unit is configured to provide a DC electric current for driving the test field source in generating the magnetic test field.

In other brachytherapy systems, for controlling a respective measurement of the magnetic test field, the test drive control unit is configured to provide the test drive control signal to the wire driving unit for positioning the test field source at one predetermined test position and for positioning the transducer at one predetermined receive position in the second external delivery channel, and the test-field-source driving unit is configured to provide an AC electric current for driving the test field source in generating the magnetic test field. In these systems, since for a given measurement of the magnetic test field, the test position and the receive position are fixed, variation in the magnetic test field are caused by the AC electric current used for driving the test-field source.

In some exemplary brachytherapy systems, test drive control unit is configured to provide the test drive control signal to the wire driving unit for consecutively positioning the transducer in a plurality of second external delivery channels, for controlling a plurality of consecutive measurements of the magnetic test field. Therefore, the detection of changes in the magnetic test field generated by the test-field source is consecutively carried out place within a plurality of delivery channels.

Regarding the quality-assurance unit 444, in some brachytherapy systems it is configured to determine a signal amplitude of the received transducer signal and of the expected transducer signal, to perform the comparison by determining a deviation measure indicative of a deviation of the signal amplitude of the received transducer signal from that of the expected transducer signal, and to provide a positioning error signal if the deviation measure exceeds a predetermined deviation threshold value.

Figure 5:
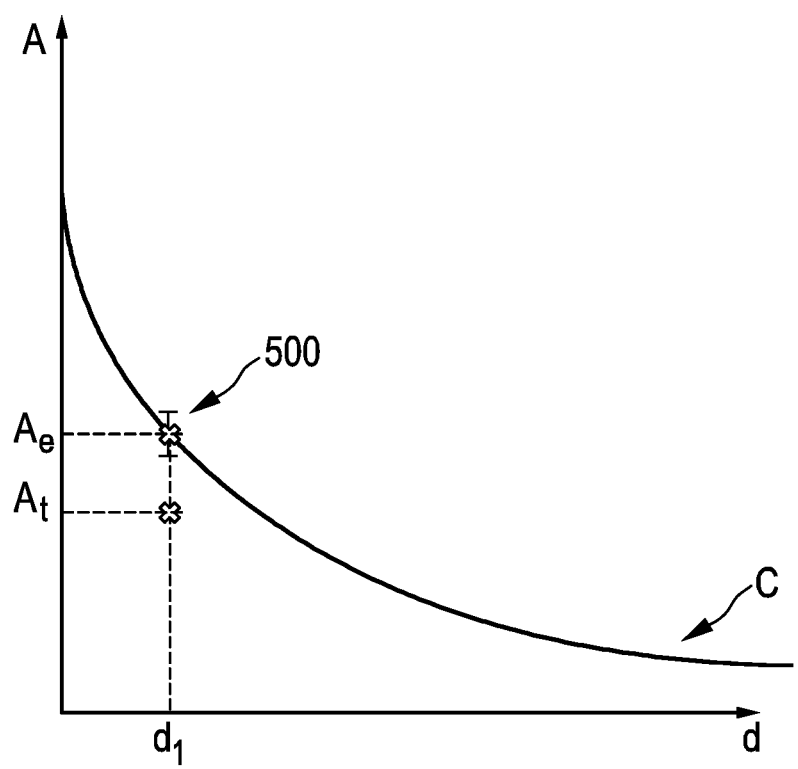
FIG. 5 shows a graph depicting the relationship between the amplitude A of a magnetic test field generated by a test field source and the distance d at which it is detected by a transducer.

This is explained with reference to FIG. 5, which shows a graph depicting the relationship between the amplitude A of the magnetic test field generated by a test field source and the distance d at which it is detected by the transducer. The quality-assurance unit uses the test position and the receive position (both in different delivery channels) to determine an expected transducer signal to be expected from the transducer when the test field source is at the test position and the transducer at the receive position separated a distance ditherefrom. A signal amplitude $A_t$ of the received transducer signal is determined, as well as an expected signal amplitude $A_e$ of the expected transducer signal. The values of the expected amplitude for any given distance lie on the curve C. However, the signal amplitude of $A_t$ of the transducer signal may not lie on said curve C due to several reasons. Some of these reasons involve assumptions that have to be made for the calculations and that relate to the material properties of the target volume. Other reasons involve an incorrect positioning, with respect to the planned therapy data, of the catheters into the target volume or even an incorrect connection of the delivery channels to the indexing unit, so that one or more delivery channels occupy swapped positions.

The quality-assurance unit is configured to perform the comparison by determining a deviation measure (e.g. the ratio between both amplitudes) indicative of a deviation of the signal amplitude $A_t$ of the received transducer signal from that of the expected transducer signal $A_e$ and to provide a positioning error signal if the deviation measure exceeds a predetermined deviation threshold value, symbolized by the error bar 500. The deviation threshold value is advantageously chosen to enable distinguishing inaccuracies in the assumptions of the material properties from other sources of error related to the position of the catheters or the connection of the delivery channels. In the current example, the deviation measure between $A_e$ and $A_t$ is larger than the deviation threshold value and a positioning error signal is provided by the quality-assurance unit to an external user to indicate that there is possibly an error in the delivering channels that should be checked before proceeding with the actual brachytherapy plan using a highly radioactive source. In case the deviation measure is lower than the deviation threshold value, a positioning-confirm signal is provided by the quality-assurance unit.

By performing a plurality of measurements of the magnetic test field at different testing and or receiving positions some brachytherapy systems are advantageously configured to provide a quality assurance signal indicative of one of a plurality of expected errors, which may include, for example, swapping of two or more given delivery channels or the incorrect positioning of a given catheter.

Some brachytherapy systems are configured to use a knowledge of the positions of the different delivery channels, and also of a respective dwelling time of a radioactive source, both according to the planned therapy data, as well as information pertaining to the generated magnetic test field and the received transducer signal to simulate signal radiation generation in one or more locations and the associated expected transducer signal in any given location. Ultimately this information can be used to select optimal locations based on position combinations that produce optimal signals in terms of, for instance, signals having highest amplitude values, or highest SNR, etc.

Figure 6:
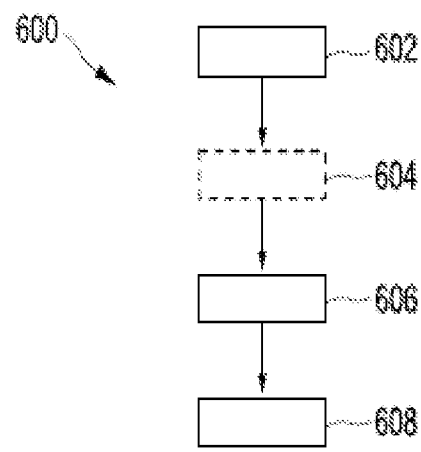
FIG. 6 shows a flow diagram of an embodiment of a method for operating an afterloader control unit of a brachytherapy system.

FIG. 6 shows a flow diagram of an embodiment of a method 600 for operating an afterloader control unit of a brachytherapy system. The method comprises controlling, in a step 602, an advance or retract motion of at least one transmit wire that is suitable for being inserted and for being driven in an external first delivery channel for positioning the test field source at a predetermined test position in the first delivery channel. Some preferred embodiments optionally comprise a step 604 (dashed box in FIG. 6) for controlling delivery of electrical drive energy to a test field source, which is arranged at a distal end region of the transmit wire, for controllably generating a magnetic test field. Further, in a step 606, the method is configured to control an advance or retract motion of at least one receive wire that is suitable for being inserted and for being driven in at least one external second delivery channel for positioning a transducer, that is arranged on the receive wire and configured to detect magnetic-field changes in the magnetic test field, at a predetermined receive position. Finally, in a step 608, the method comprises a step for receiving from the transducer a transducer signal indicative of the detected magnetic-field changes.

Figure 7:
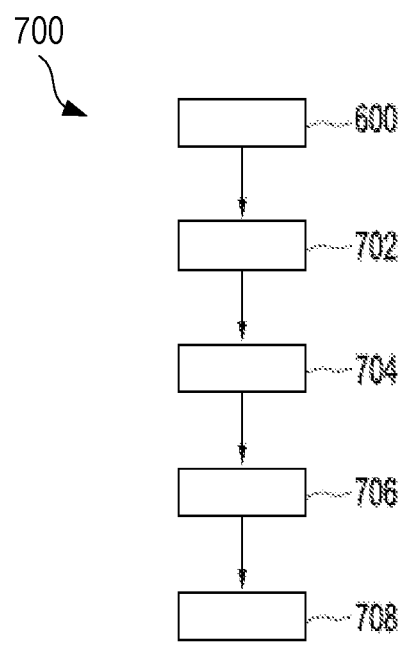
FIG. 7 shows a flow diagram of another embodiment of a method for operating an afterloader control unit of a brachytherapy system.

FIG. 7 shows a flow diagram of another embodiment of a method 700 for operating an afterloader control unit of a brachytherapy system. The method comprises the steps of method 600 and further includes a step 702 for providing planned-therapy data indicative at least of a planned radioactive-source position in the first delivery channel, a step 704 for determining, using the test position and the at least one receive position in the at least one second external delivery channel, at least one expected transducer signal to be expected from the transducer at the at least one receive position when the test field source is at the test position, a step 706 for performing a comparison of the received transducer signal with the expected transducer signal and a step 708 for providing a quality assurance signal indicative of a result of the comparison.

The invention claimed is:

1. A brachytherapy afterloader device, comprising:
at least one transmit wire that is suitable for being inserted and for being driven in an advance or retract motion in an external first delivery channel, the at least one transmit wire having a test field source, which is arranged at a distal end region of the at least one transmit wire, for controllably providing a magnetic test field;
at least one receive wire that is suitable for being inserted and for being driven in an advance or retract motion in an external second delivery channel for a measurement of the magnetic test field, the at least one receive wire having a transducer that is configured to detect magnetic-field changes in the magnetic test field and to provide a transducer signal indicative thereof via the at least one receive wire; and
a wire driving unit which is configured to controllably advance or retract the at least one transmit wire and the at least one receive wire in response to a corresponding test drive control signal.

2. The brachytherapy afterloader device of claim 1, wherein the at least one transmit wire is configured to transport electrical drive energy to the test field source and wherein the test field source is configured to generate the magnetic test field in dependence on the electrical drive energy received by the test field source.

3. The brachytherapy afterloader device of claim 2, wherein the test field source comprises a transmit coil and the transducer comprises a receive coil.

4. The brachytherapy afterloader device of claim 3, wherein the at least one transmit wire and the at least one receive wire comprise respective connecting wires that are arranged in a respective inner lumen of the at least one transmit wire and the at least one receive wire and that are arranged to electrically connect the receive coil with an external signal receiving unit for receiving the transducer signal, and the transmit coil with an external transmit-coil driving unit for delivering the electrical drive energy, respectively.

5. The brachytherapy afterloader device of claim 1, wherein the wire driving unit comprises:
a transmit-wire reel for accommodating at least a portion of the at least one transmit wire in its retracted state;
a receive-wire reel for accommodating at least a portion of the at least one receive wire in its retracted state;
a first motor configured to drive the transmit-wire reel in effectuating the advance or retract motion of the at least one transmit wire in response to a corresponding first test drive control signal; and
a second motor configured to drive the receive-wire reel in effecting the advance or retract motion of the at least one receive wire to a corresponding second test drive control signal.

6. The brachytherapy afterloader device of claim 1, further comprising:
at least one therapy wire that is suitable for being inserted and for being driven in an advance or retract motion in at least the first external first delivery channel and comprising a radioactive source, which is arranged at a distal end region of the at least one therapy wire; wherein
the wire driving unit is configured to controllably advance or retract the at least one therapy wire in response to a corresponding therapy drive control signal.

7. A brachytherapy system, comprising:
a brachytherapy afterloader device, the brachytherapy afterloader device comprising:
at least one transmit wire that is suitable for being inserted and for being driven in an advance or retract motion in an external first delivery channel, the at least one transmit wire having a test field source, which is arranged at a distal end region of the at least one transmit wire, for controllably providing a magnetic test field;
at least one receive wire that is suitable for being inserted and for being driven in an advance or retract motion in an external second delivery channel for a measurement of the magnetic test field, the at least one receive wire having a transducer that is configured to detect magnetic-field changes in the magnetic test field and to provide a transducer signal indicative thereof via the at least one receive wire; and
a wire driving unit which is configured to controllably advance or retract the at least one transmit wire and the at least one receive wire in response to a corresponding test drive control signal;
and
an afterloader control unit, the afterloader control unit comprising:
a test drive control unit configured to provide, using planned-therapy data indicative of at least a planned radioactive-source position in the external first delivery channel, the test drive control signal to the wire driving unit for positioning the test field source at a test position (T) depending on the planned radioactive-source position in the external first delivery channel, and for positioning the transducer at at least one receive position (R) in the external second delivery channel;
a signal receiving unit that is configured to sample the transducer signal provided by the transducer in the at least one receive position in the second external second delivery channel via the at least one receive wire; and
a quality-assurance unit that is connected with the signal receiving unit and configured to:
determine, using the test position and the at least one receive position in the external second delivery channel, at least one expected transducer signal to be expected from the transducer at the at least one receive position when the test field source is at the test position, and perform a comparison of the transducer signal with the at least one expected transducer signal and provide a quality assurance signal indicative of a result of the comparison.

8. The brachytherapy system of claim 7, wherein the brachytherapy system further comprises:
a test-field-source driving unit that is configured to provide the electrical drive energy via the at least one transmit wire for driving the test field source in generating the magnetic test field at the test position.

9. The brachytherapy system of claim 8, wherein, for controlling a respective measurement of the magnetic test field:
the test drive control unit is configured to provide the test drive control signal to the wire driving unit for positioning the test field source at one predetermined test position and for positioning the transducer at one predetermined receive position in the external second delivery channel; and wherein
the test-field-source driving unit is configured to provide an AC electric current for driving the test field source in generating the magnetic test field.

10. The brachytherapy system of claim 7, wherein, for controlling a respective measurement of the magnetic test field, the test drive control unit is configured to provide the test drive control signal to the wire driving unit suitable:
for positioning the test field source at one predetermined test position and for consecutively positioning the transducer at a plurality of receive positions in the external second delivery channel; or
for consecutively positioning the test field source at a plurality of predetermined test positions and for positioning the transducer at one receive position in the external second delivery channel; or
for consecutively positioning the test field source at a plurality of predetermined test positions and for simultaneously and consecutively positioning the transducer at a plurality of receive positions in the external second delivery channel.

11. The brachytherapy system of claim 7, wherein the test drive control unit is configured to provide the test drive control signal to the wire driving unit for consecutively positioning the transducer in a plurality of external second delivery channels, for controlling a plurality of consecutive measurements of the magnetic test field.

12. The brachytherapy system of claim 7, wherein the quality-assurance unit is configured to:
determine a signal amplitude of the transducer signal and of the at least one expected transducer signal;
perform the comparison by determining a deviation measure indicative of a deviation of the signal amplitude of the transducer signal from that of the at least one expected transducer signal; and
provide the quality assurance signal as a positioning error signal if the deviation measure exceeds a predetermined deviation threshold value.

13. A method for operating an afterloader control unit of a brachytherapy system, the method comprising:
controlling an advance or retract motion of at least one transmit wire that is suitable for being inserted and for being driven in an external first delivery channel for positioning a test field source at a predetermined test position in the external first delivery channel;
controlling an advance or retract motion of at least one receive wire that is suitable for being inserted and for being driven in at least one external second delivery channel for positioning a transducer, that is arranged on the at least one receive wire and configured to detect magnetic-field changes in a magnetic test field, at a predetermined receive position; and
receiving from the transducer a transducer signal indicative of the detected magnetic-field changes.

14. A method according to claim 13, further comprising:
providing planned-therapy data indicative at least of a planned radioactive-source position in the external first delivery channel;
determining, using the predetermined test position and the predetermined receive position in the at least one external second delivery channel, at least one expected transducer signal to be expected from the transducer at the predetermined receive position when the test field source is at the predetermined test position;
performing a comparison of the received transducer signal with the at least one expected transducer signal; and
providing a quality assurance signal indicative of a result of the comparison.

* * * * *